United States Patent
Skousen et al.

(10) Patent No.: US 11,903,852 B2
(45) Date of Patent: Feb. 20, 2024

(54) MULTI-STAGE STENT DEVICES AND ASSOCIATED METHODS

(71) Applicant: Brigham Young University, Provo, UT (US)

(72) Inventors: Darrell Skousen, Lehi, UT (US); Anton E. Bowden, Lindon, UT (US)

(73) Assignee: Brigham Young University, Provo, UT (US)

( * ) Notice: Subject to any disclaimer, the term of this patent is extended or adjusted under 35 U.S.C. 154(b) by 93 days.

(21) Appl. No.: 15/999,254

(22) PCT Filed: Feb. 17, 2017

(86) PCT No.: PCT/US2017/018529
§ 371 (c)(1),
(2) Date: Aug. 17, 2018

(87) PCT Pub. No.: WO2017/143302
PCT Pub. Date: Aug. 24, 2017

(65) Prior Publication Data
US 2020/0330250 A1  Oct. 22, 2020

Related U.S. Application Data

(60) Provisional application No. 62/296,363, filed on Feb. 17, 2016.

(51) Int. Cl.
*A61F 2/915* (2013.01)

(52) U.S. Cl.
CPC ...... *A61F 2/915* (2013.01); *A61F 2210/0014* (2013.01); *A61F 2240/001* (2013.01); *A61F 2250/0031* (2013.01)

(58) Field of Classification Search
CPC .... A61F 2/915; A61F 2/82; A61F 2250/0031; A61F 2250/003; A61F 2002/9155
See application file for complete search history.

(56) References Cited

U.S. PATENT DOCUMENTS

| | | |
|---|---|---|
| 5,522,876 A | 6/1996 | Rusink |
| 5,957,975 A | 9/1999 | Lafont et al. |
| 6,663,664 B1 | 12/2003 | Pactti |
| 8,764,813 B2 * | 7/2014 | Jantzen ............ A61L 31/16 623/1.13 |
| 2002/0065546 A1 * | 5/2002 | Machan ............ A61F 2/07 623/1.13 |
| 2006/0224235 A1 | 10/2006 | Rucker |
| 2007/0219626 A1 * | 9/2007 | Rolando ............ A61F 2/91 623/1.16 |
| 2012/0310329 A1 | 12/2012 | Omura et al. |
| 2014/0094900 A1 * | 4/2014 | Bowden ............ A61F 2/844 623/1.16 |
| 2015/0164664 A1 | 6/2015 | Skousen et al. |
| 2015/0265441 A1 | 9/2015 | Weber |

* cited by examiner

*Primary Examiner* — Christopher D. Prone
(74) *Attorney, Agent, or Firm* — Thorpe North & Western, LLP; Todd B. Alder (57) ABSTRACT

A multi-stage stent including a stent body and a bio-erodible material is provided. The stent body can be compressed in an initial state and the bio-erodible material can be coupled to the stent body in a configuration that holds the stent body in an expanded first state, following a first stage expansion from the initial state upon deployment of the stent body. Upon erosion of the bio-erodible material the stent body is released from the first state to expand further in a second stage expansion to a second state.

10 Claims, 8 Drawing Sheets

Day 0

FIG. 10A

Day 12

MULTI-STAGE STENT DEVICES AND ASSOCIATED METHODS

CROSS-REFERENCE TO RELATED APPLICATIONS

This application is a U.S. nationalization under 35 U.S.C. § 371 of International Application No. PCT/US17/18529, filed Feb. 17, 2017, which claims the benefit of U.S. Provisional Application No. 62/296,363, filed on Feb. 17, 2016, each of which is incorporated herein by reference in its entirety.

BACKGROUND

Figure 1:
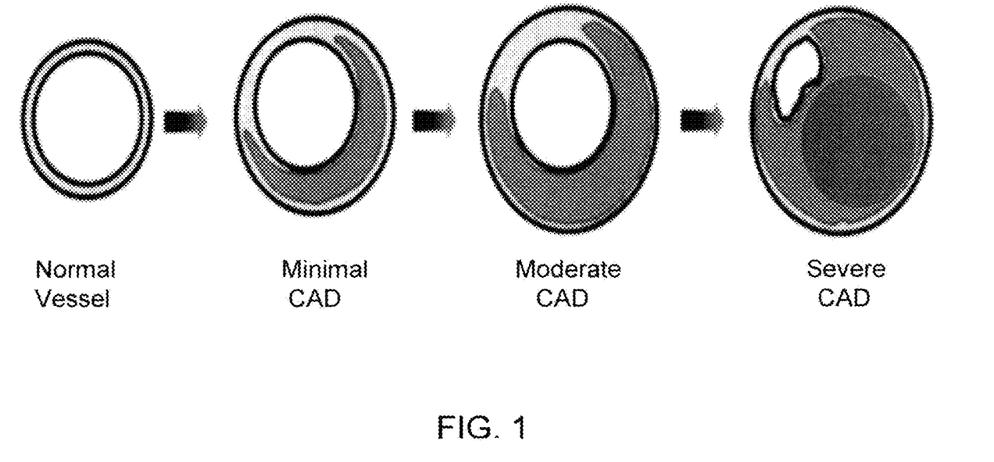
FIG. 1 illustrates a schematic showing plaque build-up in the interior artery wall in different stages of CAD.

One leading cause of death in the United States is heart disease. Coronary artery disease (CAD), the most common type of heart disease, kills over 370,000 people every year. In CAD, plaque and minerals accumulate in the interior of an artery, as shown in FIG. 1, thereby creating a restriction in the artery that reduces blood flow to the heart. This reduction in blood flow can lead to heart failure and death. A minimally invasive procedure known as percutaneous coronary intervention (PCI) it is commonly used to open such narrow restrictions in coronary arteries to thereby treat CAD.

There are two major complications associated with PCI, thrombosis (blood clots) and restenosis (re-narrowing of the interior of the artery). Following PCI, blood-thinning drugs can be administered to treat thrombosis. Restenosis, on the other hand can, be more difficult to treat. Restenosis can occur by three different mechanisms, including early elastic recoil, negative arterial remodeling, and/or neointimal formation. Early elastic recoil is the tendency of the artery to revert to its pre-PCI shape, and is a result of the elastic properties of the artery. Negative arterial remodeling is a narrowing of the outer diameter of a section of the artery compared to the outer diameter of the artery at an adjacent section as the artery wall moves inward. Negative remodeling is believed to be a response to hemodynamic changes and humoral factors, and neointimal formation is the proliferation and migration of vascular smooth muscle cells, resulting in a thickening of arterial walls that reduces the interior volume of the affected section of the artery, both of which can result in late lumen loss in PCI. During PCI, a cylindrical stent is implanted to open a narrow section of the artery. Stents can prevent elastic recoil and negative arterial remodeling; however, neointimal formation can still lead to restenosis.

These drawings are provided to illustrate various aspects of the invention and are not intended to be limiting of the scope in terms of dimensions, materials, configurations, arrangements, or proportions unless otherwise limited by the claims.

DETAILED DESCRIPTION

An initial overview of technology embodiments is provided below and specific technology embodiments are then described in further detail. This initial summary is intended to aid readers in understanding the technology more quickly, but is not intended to identify key or essential technological features, nor is it intended to limit the scope of the claimed subject matter.

In one example presented herein, is a multi-stage stent including a stent body and a bio-erodible material. The stent body can be compressed in an initial state and the No-erodible material can be coupled to the stent body in a configuration that holds the stent body in an expanded first state following a first stage expansion from the initial state upon deployment of the stent body. Upon erosion of the bio-erodible material, the stent body is released from the first state to expand further in a second stage expansion to a second state.

Also presented herein is a method of making a multi-stage stent. In one example, such a method can include forming a stent body having a structural configuration to be expanded from an initial compressed state to a fully expanded second state. The method can further include compressing the stent body to the initial compressed state and applying a bio-erodible material to the stent body in a configuration to hold the stent body in an expanded first state following a first expansion stage that is an intermediate between the initial compressed state and the second state.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention. Although the following detailed description contains many specifics for the purpose of illustration, a person of ordinary skill in the art will appreciate that many variations and alterations to the following details can be made and are considered included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that, which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in this specification, like "comprising" or "including," it is understood that direct support should be afforded also to "consisting essentially of" language as well as "consisting of" language as if stated explicitly and vice versa.

"The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, comparative terms such as "increased," "decreased," "better," "worse," "higher," "lower," "enhanced," and the like refer to a property of a device or component, that is measurably different from other devices or components, in a surrounding or adjacent area, in a single device or in multiple comparable devices, in a group or class, in multiple groups or classes, or as compared to the known state of the art.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, "bio-erodible material" refers to a material that erodes over time in a biological environment. In one example, a biological environment can be a physiological environment, such as inside of a living subject. In another example, a biological environment can be in the bloodstream, such as, for example, the interior of an artery or the interior of a vein.

As used herein, "subject" refers to a mammal that may benefit from a stent implantation. Examples of subjects include humans, and may also include other mammals such as horses, pigs, cattle, dogs, cats, rabbits, aquatic mammals, and the like.

As used herein, "coupled" refers to a relationship of physical connection or attachment between one item and another item, and includes relationships of either direct or indirect connection or attachment. Any number of items can be coupled, such as materials, components, structures, layers, devices, objects, etc.

As used herein, "directly coupled" refers to a relationship of physical connection or attachment between one item and another item where the items have at least one point of direct physical contact or otherwise touch one another. For example, when one layer of material is deposited on or against another layer of material, the layers can be said to be directly coupled.

Objects or structures described herein as being "adjacent to" each other may be in physical contact with each other, in close proximity to each other, or in the same general region or area as each other, as appropriate for the context in which the phrase is used.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

While the discussion herein is primarily directed to stents placed in coronary arteries, those skilled in the art would understand that the principles discussed herein apply to other types of stents, such as esophageal stents, biliary stents, vascular stents, ureteral stents, prostatic stents, glaucoma drainage stents, duodenal stents, colonic stents, pancreatic stents, and the like. The stent design presented herein should not be limited to coronary artery stents.

Example Embodiments

In one example, a multi-stage stent is provided that can be inserted into a subject at a location where an expandable stent can provide a benefit. The multi-stage stent is inserted, in an artery of a subject, for example, in a physical configuration whereby the stent body is in an initial compressed state. Once in position, deployment of the stent can be initiated through a variety of nonlimiting techniques, which causes the stent body to expand from the initial compressed state due to the elastic potential energy that was stored upon compression. More specifically, upon release from the initial compressed state, the stored elastic potential energy returns the stent body toward its original expanded state. The expansion of the stent body can be halted at any point between the initial compressed state and the fully expanded state through the use of an expansion stop coupled to the stent body in a configuration that physically blocks further expansion. In one nonlimiting example, a stent body expands until the changing physical configuration of the stent body engages an expansion stop, thus halting expansion. Such expansion stops can be positioned according to different configurations to also facilitate multiple states or points where expansion is halted, thus allowing stent designer to control the dynamics of stent deployment over time. While a stent is described herein as having various expansion stages with various non-expanding states therebetween, such is intended to be nonlimiting, and the present scope includes any number of expansion stages with intervening non-expanding states.

The disclosed multi-stage expansion permits the expansion dynamics of a stent, positioned across a blockage within an artery or other biological passage, to be tailored to achieve a desired result. In other words, compressed stent can be design to deploy according to any number of desired expansion profiles. Thus, the physical configuration of an expansion stop, the physical properties of material or materials used to form the expansion stop, and the manner in which the expansion stop is coupled to a stent body, provides a broad degree of configurability to the expansion dynamics of the stent body when use. Over time, the expansion stop material bio-erodes sufficiently to release the stent body from an expansion-paused state, which causes the stent body to expand further, either gradually over time or rapidly, in some examples to its fully expanded state. Such a pause in expansion, followed by a further expansion at a later time, can reduce the trauma associated with implantation, reduce the incidence of complications that occur due to restenosis, such as the inward growth of the artery wall.

Figure 2:
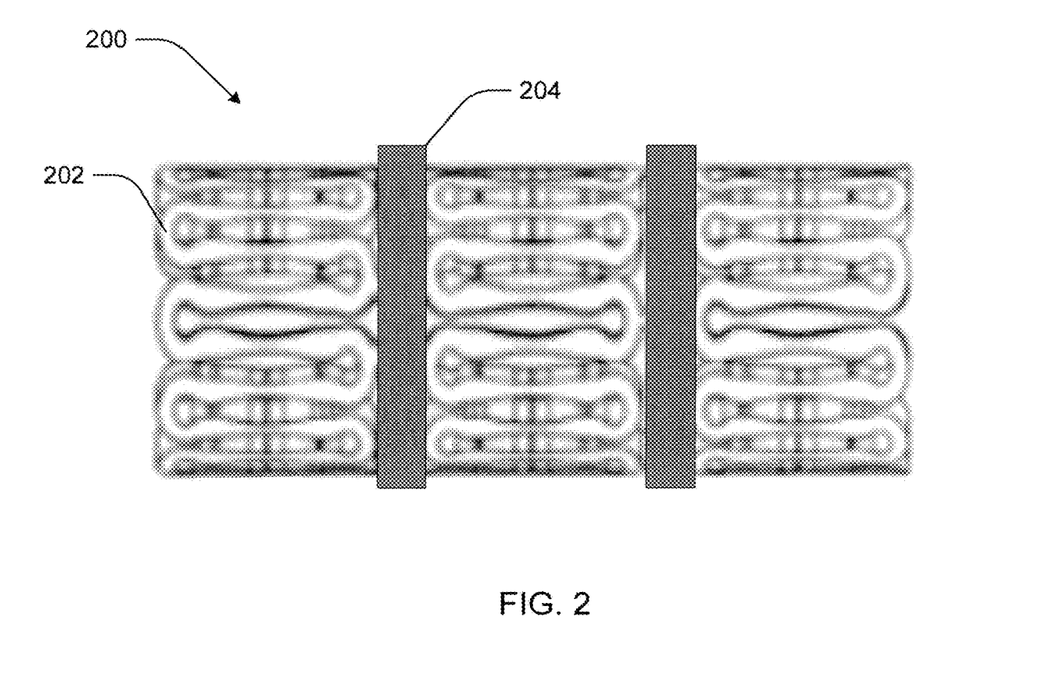
FIG. 2 is an illustration of a multi-stage stent in accordance with an example presented herein.

As shown in FIG. 2, one example of a multi-stage stent 200 can include a stent body 202 and a bio-erodible or bio-resorbable material 204. The stent body can be of any configuration that allows the stent body to be compressed and subsequently expanded back to its fully extended original shape. Such compression and expansion of the stent body can be a product of the material used in the stent body, the configuration of the structures making up the stent body, or both. Regarding configurations of stent body structures, various nonlimiting examples can include coil patterns, zigzag patterns, helical patterns, spiral patterns, woven patterns, individual ring patterns, sequential ring patterns, geometric cell patterns, or the like, including combinable combinations thereof.

Figure 3:
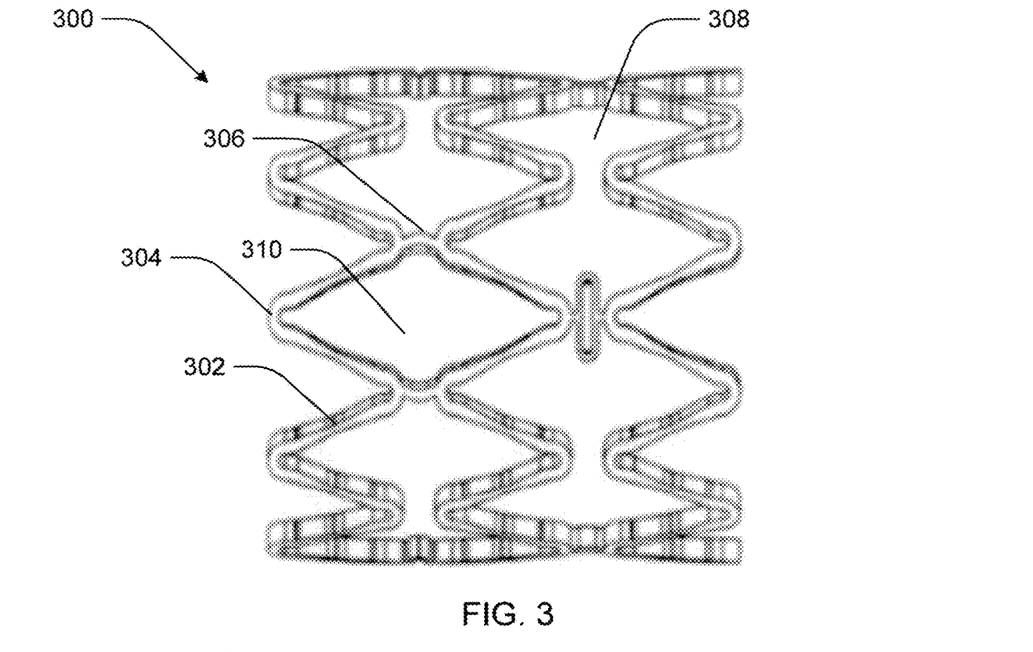
FIG. 3 is an illustration of an open cell and a closed cell design in accordance with an example of a stent body presented herein.

In one example, a stent body can be sufficiently flexible to allow the stent to conform to the motions of the artery into which it has been inserted. Two non-limiting design concepts can be utilized to allow a range of flexibilities to a stent include the design of the cell pattern and the design of the strut dimensions making up the stent body. Cell pattern designs can vary, and can include open cells, closed cells, or a combination open and closed cells. One useful design can include a cell pattern that is a combination open-closed pattern, as is shown in FIG. 3. The stent body 300 in this example includes a plurality of struts 302 coupled together by one or more end radii 304, and arranged in rows of zigzag patterns that are coupled together by connecting members 306. As such, the various struts, end radii, connecting members, etc., generally form into a contiguous mesh pattern (generally cylindrical in shape) that defines the cell pattern of the sent body. In the case of FIG. 3, the stent body includes both open cells 308 and closed cells 310. The struts 302 can be optimized for flexibility through the reduction of material along the length of the strut, and an increase of material at the radii. In other words, the struts are thicker at each end, and taper to the middle. This distribution of material mass allows the strut to be compensated for stiffness through the reduction of mass in the region that is least affected by bending stress. The open-closed cell pattern maintains the stent body shape, and allows for complex motions, such as contracting while twisted and bent, for example. Additionally, in one example the connecting members 306 are slightly thinner than the struts 302, which provides an extra degree of motion when the stent undergoes a twisting transformation.

A stent body can comprise any material, material composite, alloy, or the like, that can be utilized as a stent and resistant corrosion or can be made resistant to corrosion, in a physiological environment. The stent material additionally should allow for elastic compression, such that upon release from compression, will cause the stent body to expand to its original shape. Furthermore, the material should be biocompatible, and thus be biologically inert when placed in a biological environment. Nonlimiting examples of such materials can include carbon nanotubes, carbon infiltrated carbon nanotubes, various shape memory materials, polymers, bio-absorbable polymers, steel, and stainless steel, including various alloys and composites with materials such as nickel, chromium, magnesium, zinc, tantalum, tin, and the like. In one example, a stent body can include a carbon nanotube material, which in some cases can be infiltrated with an infiltrant material, such as carbon, pyrolytic carbon, or the like.

In yet another example, a stent body material can include a shape memory material. Shape memory materials generally refer to materials that can be deformed and reverted to their original shape, and can include various metal alloys, polymers, and combinations thereof. It noted that the shape memory materials appropriate for the present disclosure do not request heating to return the material to its original state. Exemplary shape memory materials can include, but are not limited, various metal alloys of silver, cadmium, gold, aluminum, nickel, tin, zinc, iron, platinum, magnesium, copper, iron, cobalt, gallium, titanium, niobium, hafnium, and/or palladium. In one example, stent body material can include nitinol, a nickel/titanium alloy. Nitinol, or any stent body material, can be processed to further improve corrosion resistance. In one example, nitinol can be processed by fine surface finishing. In another example, a shape memory material can be a shape memory polymer, such as, for example, polyurethane, polyethylene, polypropylene, polyamide, polyethylene terephthalate, polytetrafluoroethylene, nylon, ethylene tetrafluoroethylene, polyethylene oxide, polystyrene and poly(1,4-butadiene) block copolymers, polynorbornene, polyhedral oligosilsesquioxane, and the like.

Upon placement of a stent in an artery, the expansion from the initial compressed state can be initiated manually or automatically. For example, a medical practitioner placing the stent can ensure that the stent is in a proper position, and then manually activate the stent to begin a first stage expansion from the initial compressed state to a first expansion state, where expansion is halted by one or more expansion stops. This first expansion stage can occur rapidly following the manual activation, or it can occur gradually over time. The term "first stage" refers to an expansion phase of a stent body from an initial compressed state to an expansion position where expansion is halted at a first state that is intermediate between the initial compressed state and a fully-expanded state. Additionally, the term "second stage" refers to an expansion phase of a stent body from the first state to a further expansion position, or second state. In some examples, the second state can be a fully-expanded state. In other examples, the second stage can be followed by one or more subsequent expansion stages, such as a third stage, a fourth stage, and so on.

Figure 4:
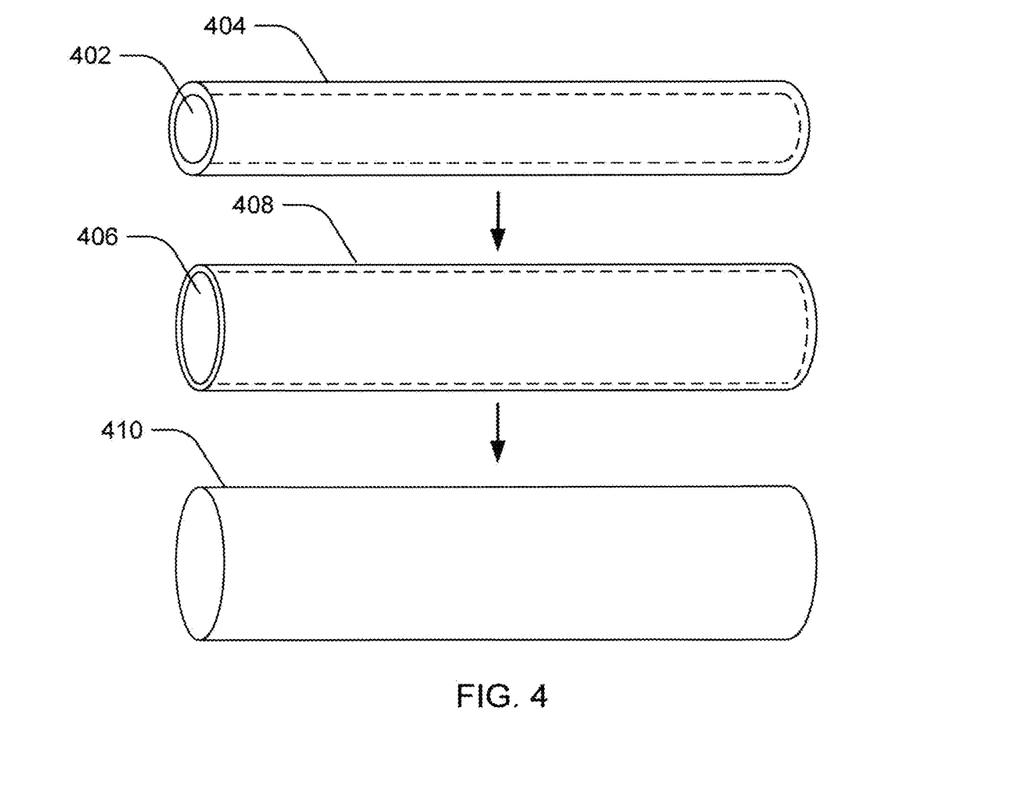
FIG. 4 is an illustration of the expansion of a multi-stage stent having a bio-erodible material applied as a coating around the exterior of a stent body, in accordance with an example presented herein.

In one example, as is shown in FIG. 4, a stent body 402 in a compressed state is coated with a bio-erodible coating 404. The coating 404 contains the stent body 402 in the compressed state during implantation, and should thus have an erosion time that is at least greater that the maximum expected time for an implantation procedure, in order to avoid expansion of the stent during implantation. As the coating erodes 408 and begins to thin, the stent body begins to expand 406 due to the stored elastic potential energy exerting radial force against the coating. The coating then thins sufficiently to allow the stent body to expand to its fully expanded state 410, or to the state of expansion allowed by any associated expansion stops.

As has been described, one or more expansion stops can be coupled to the stent body to halt or otherwise modify the expansion characteristics of the stent. An expansion stop can have any physical configuration that provides a stop against expansion of the stent body. In some examples, it can be beneficial to utilize a design and/or material for the expansion stop that ensure the expansion stop material remains coupled to the stent body material until fully resorbed, in order to avoid loose material particles within the artery. Various configurations of expansion stops can include, without limitation, spot welds, geometric links, composite beams, hook and eye linkages, bands, mechanical locks, bio-resorbable pin and track configurations, coatings, and the like, including combinations thereof. For example, spot welds of expansion material can be applied to the stent body, which can then have a coating deposited thereon as a double expansion stop mechanism.

Figure 5:
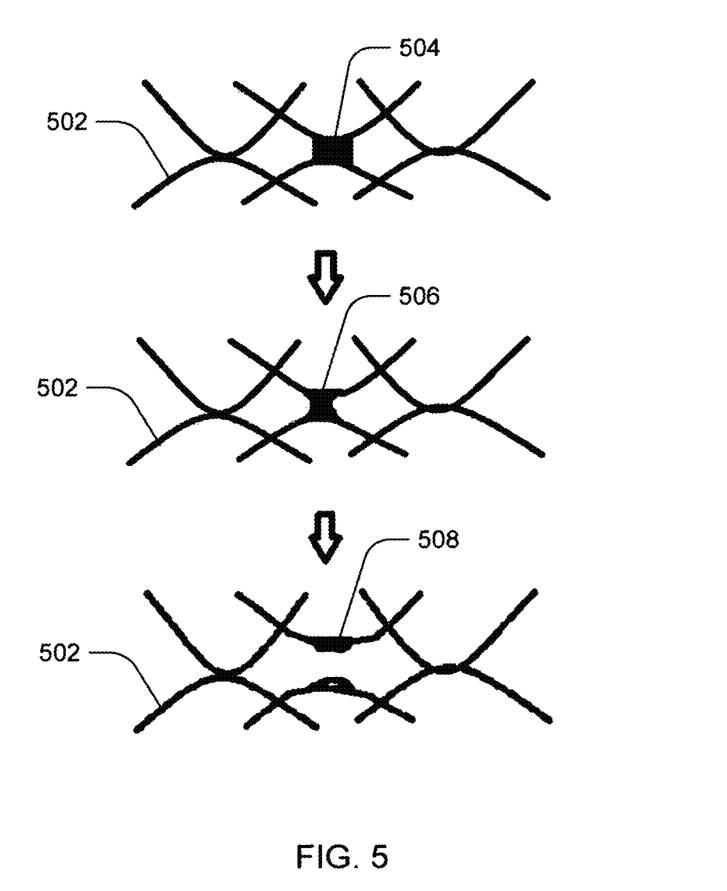
FIG. 5 is an illustration of a multi-stage stent having a bio-erodible material applied as spot welds on a stent body in accordance with an example presented herein.

FIG. 5 shows an example of a stent body 502 having a plurality of expansion stops 504 (only one shown) spot welded, or otherwise applied, to discrete locations on the stent body 502. On implantation, the stent body expands through the first expansion stage, which is halted by the expansion stops at the first state. As the plurality of expansion stops begin to erode 506, the radial forces from the stored elastic potential energy in the stent body begin to overcome the tensile strengths of the expansion stops, and the stent body starts the second expansion stage. As the erosion continues, individual expansion stops break 508, thus increasing the tensile force on the remaining expansion stops, further increasing the expansion until the stent body reaches a second state.

Figure 6:
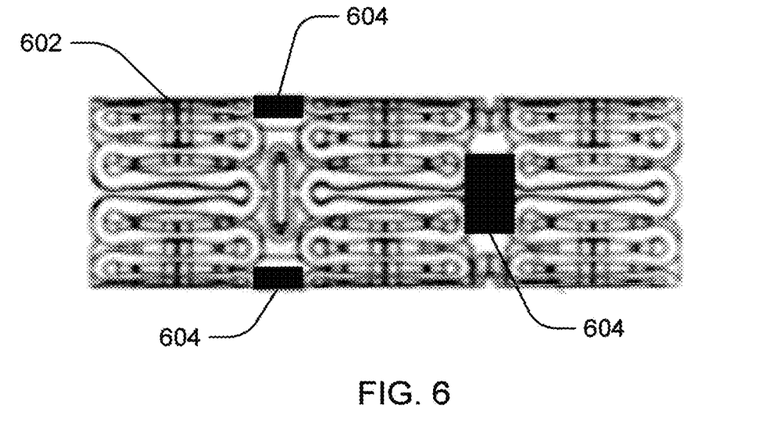
FIG. 6 is an illustration of a multi-stage stent having a bio-erodible material applied as expansion stop on a stent body in accordance with an example presented herein.

FIG. 6 shows another example of a stent body 602 in a compressed state, and having a plurality of expansion stops 604 positioned at discrete locations to maintain the stent body 602 at the first expansion state. As has been described, the expansion stop can be configured as various mechanical attachments, external bands, composite beams, links, and the like. In one example, an expansion stop can be a mechanical attachment that allows for a controlled expansion of the stent body. In another example, one or more expansion stops can be external bands that run at least partially around the stent body circumference, at least partially along the length of the stent body, or a combination thereof. Multiple bands can be used to allow for a gradual expansion for the stent body, and in some cases the bands can be of varying thicknesses to allow variation in the expansion dynamics. In another example, an expansion stop can be link that can, in one example, connect open cells in an open cell design of a stent body. As these link expansion stops erode, the stent body expands over time to the second state. In one example, a stent body can radially expand substantially uniformly along an elongate axis during expansion from the first state to the second state.

The degree of expansion between the first state and the second state can vary, depending on the design and intended expansion dynamics of the stent. In one example, however, the outside diameter of a stent at the first state can be about 70% to about 90% of the outside diameter at the second state. In another example, the outside diameter of a stent at the first state can be about 75% to about 85% compared to the second state. In a further example, the outside diameter of a stent at the first state can be about 80% of compared to the second state.

Bio-erodible (or bio-resorbable) materials can erode in a biological environment over a period of time that allows the potential negative side effects of stent implantation to be avoided or at least minimized. In one example, a bio-erodible material can erode over a period of time ranging from about one weeks to about eight weeks. In another example, the bio-erodible material can erode over a period of time ranging from about two weeks to about six weeks. In a further example, the bio-erodible material can erode over a period of time ranging from about three weeks to about six weeks.

The expansion of a stent body upon release can be gradual or rapid, depending on the stent design and the bio-erodible material properties that affect erosion. Factors such as the physical nature of the material, the thickness, location, and exposure of the material can play roles in the erosion dynamics. In one example, the stent body can radially expand substantially uniformly along an elongate axis during expansion from the first state to the second state. Once an expansion stop substantially erodes, the stent body can expand from the first state to the second state as the elastic potential energy stored in the stent body from the initial compression is released. In one example, the second state can be the original or fully expanded state of the stent body. In yet other examples, the second state can be an intermediate state, and further expansion can occur by incorporating a slower eroding second bio-erodible material on the stent body, or by incorporating a thicker application of the bio-erodible material at discrete locations on the stent body.

Bio-erodible materials can include any biocompatible material that erodes when placed in a biological environment. Nonlimiting examples of bio-erodible materials can include polyglycolide (PGA), polylactic acid (PLA), poly-DL-lactide (PDLLA), poly(glycolide-co-DL-lactide) (PGDLLA), poly(DL-lactide-co-glycolide (PDLGA), poly(lactic-co-glycolic acid) (PLGA), calcium triphosphate, tricalcium phosphate, cyanoacrylate, and magnesium, including composites, and combinations thereof. In one example, the bio-erodible material can be PDLGA. The composition of PDLGA can be varied to achieve various erosion profiles. In one example, however, the PDLGA can have a ratio of DL-lactic acid to glycolic acid that ranges from about 1:1 to about 6:1. In another example, the DL-lactic acid to glycolic acid ratio of the PDLGA can be about 3:1. A bio-erodible material can thus be selected such that erosion occurs within a desired time period.

Bio-erodible material can be applied to a stent body as a coating, as an expansion stop coupled to one or more discrete locations on a stent body, or it can be applied as a combination thereof. When a bio-erodible material is applied as a coating, the coating can have a uniform thickness or can be unevenly distributed so as to allow for controlled erosion of the bio-erodible material at specific locations along the stent body prior to the erosion of the bio-erodible material at other locations on the stent body. The distribution of the coating and the thickness of the coating can allow for controlled erosion and subsequent expansion of the stent body. For example, a coating can be placed about the exterior of the stent body, in bands around the exterior of the stent body, along sides of struts of a stent body, can be dip coated or otherwise deposited onto the stent body by any known deposition methods (e.g., CVD, PVD, etc.). In one example, the coating can be applied to a thickness ranging from about 100 nm to about 500 microns, or from about 500 nm to about 100 microns, or from about 1 micron to about 100 microns, or from about 5 microns to about 50 microns, or from about 2 microns to about 25 microns.

In some examples, a stent can be further coated and/or infused with a material that provides a beneficial property to the stent. For example, a stent can be coated or infused with a drug that, in one example, can thin the blood and/or reduce the incidence of blood clotting. In another example, a stent can be coated or infused with a bactericide, biocide, and/or a material that resists bacterial adhesion. In a further example, a stent can be coated or infused with a pain-relieving agent or other drug related to the comfort of the subject. In yet another example, a stent can be coated or infused with an agent that reduces the incidence of inner arterial wall growth around the stent body.

Figure 7A:
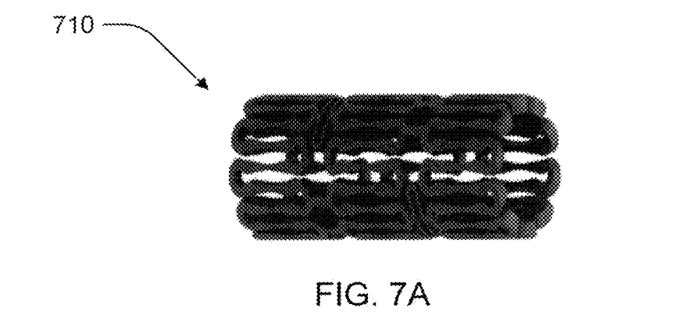
FIG. 7A is an illustration of a multi-stage stent in an initial compressed state in accordance with an example presented herein.
Figure 7B:
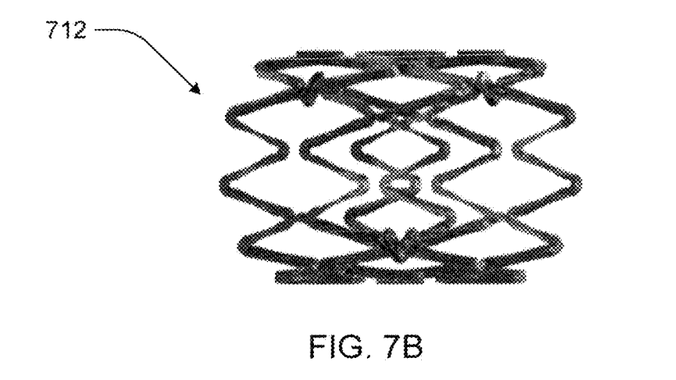
FIG. 7B is an illustration of a multi-stage stent in a first state in accordance with an example presented herein.
Figure 7C:
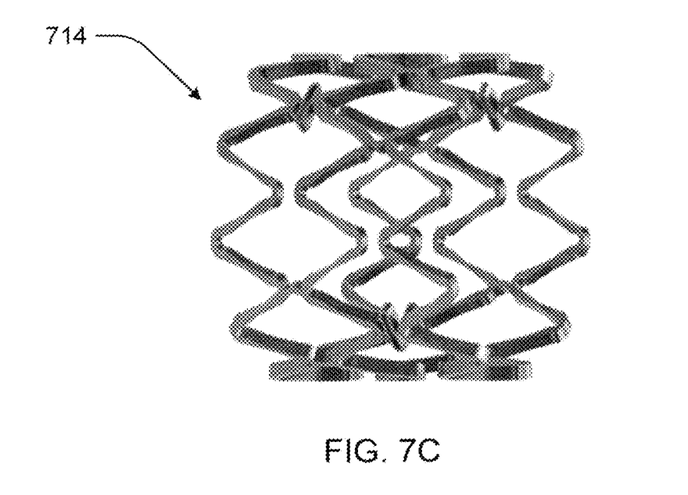
FIG. 7C is an illustration of a multi-stage stent in a second state in accordance with an example presented herein.

As previously mentioned, various components of a stent body allow for the compression and expansion of the stent body. FIGS. 7A-7C provide an overview of the fixed positions/states of a stent body throughout expansion. FIG. 7A shows a stent body in an initial compressed state 710. As the stent body expands 712, as shown in FIG. 7B, the stent body increases in diameter and shortens in length, a trend which continues until the stent body is fully expanded, as shown in FIG. 7C.

The outside diameter of a multi-stage stent in a fully expanded state can be slightly larger than the interior the artery being treated. On average, coronary arteries, for example, have an inside diameter of about 3 mm. In one example, a fully expanded multi-stage stent, as presented herein, can have an exterior diameter ranging from about 2.5 mm to about 3.5 mm. In another example, a fully expanded multi-stage stent can have an exterior diameter of about 3.3 mm.

The thickness of a stent body can also be a useful design factor. In general, stent bodies should be thick enough to prevent failure from breaking, and yet thin enough to be flexible and to function in a coronary artery. In one example, a stent body can have a thickness ranging from about 50µ to about 140µ. In another example, the thickness can range from about 75µ to 125µ. In a further example, the thickness can range from about 90µ to about 110µ.

Figure 8:
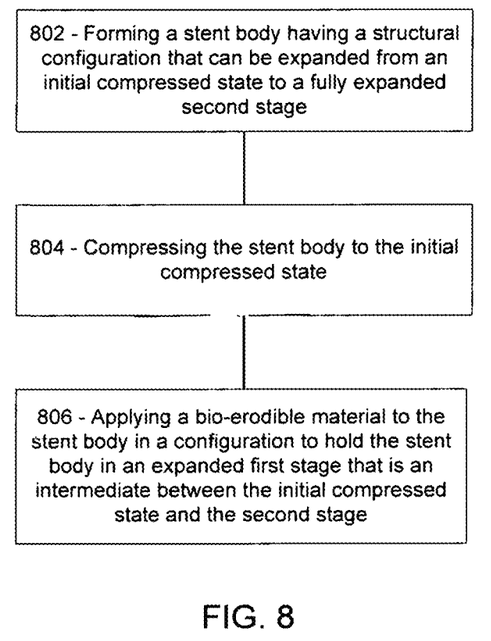
FIG. 8 shows steps of a method for making a multi-stage stent in accordance with an example presented herein.

Also provided, is a method of making a multi-stage stent. In one example, as shown in FIG. 8, such a method can include 802 forming a stent body having a structural configuration that can be expanded from an initial compressed state to a fully expanded second state, 804 compressing the stent body to an initial compressed state, and 806 applying a bio-erodible material to the stent body in a configuration to hold the stent body in an expanded first state that is an intermediate between the initial compressed state and the second state. In one example of the method, a stent body can be formed in an expanded state.

A stent body precursor can also be used in forming the stent body. In one example, forming a stent body can include removing material from a stent body precursor to form an open-closed cell design pattern. A stent body precursor can be modified in a variety of manners to create the stent body. Nonlimiting examples include laser ablation, chemical etching, mechanical abrasion, and the like. Utilizing a stent body precursor can allow for complex stent body designs that may facilitate the integration of bio-erodible materials at very fine tolerances.

In other examples, forming a stent body can include depositing a stent body material onto a deposition support substrate. Deposition can include various PVD and CVD processes, as well as other growth techniques that involve layer growth, nanotube growth, and the like. In one example, the deposition support substrate can be subsequently removed following deposition of the stent body material. In yet another example, the stent body can be 3D printed.

In one specific example, a multi-stage stent can include a stent body formed of nitinol and a bio-erodible material can of PDLGA.

EXAMPLES

The following examples illustrate the embodiments of the disclosure that are presently best known. However, it is to be understood that the following are examples, which should not be seen as limiting.

Example 1

Degradation Testing for PLA and TCP

Testing was conducted to determine the rate at which a coating of polylactic acid (PLA) or a coating of a 2:1 mixture of tri-calcium phosphate cyanoacrylate (TCP) erodes. Ten pieces of nitonol with a 3 mm diameter were coated with TCP at a thickness of 1.5 mm or 3 mm and 8 pieces of nitonol with a 3 mm were coated with PLA at a thickness of 1.5 mm or 3 mm. The coated wires were then placed in a continous flow tank containing an Earle's balanced salt solution (EBSS), that was replaced every 14 days. A SeaFlow aquatic pump (Model SFDEP1-012-035-21) was connected to the system to induce flow at a flow rate of 0.8 L/min and simulate blood flow of a coronary artery.

TABLE 1

EBSS and Plasma Compositions

| Component | EBSS Composition | Plasma Composition |
|---|---|---|
| $Na^+$ | 144 | 140 |
| $K^+$ | 5.4 | 5 |
| $Mg^{2+}$ | 0.4 | 1 |
| $Ca^{2+}$ | 1.5 | 2.5 |
| $Cl^-$ | 125 | 100 |
| $H_2PO_4^-$ | 1.0 | 0.8 |
| $SO_4^{2-}$ | 0.4 | 0.5 |
| $HCO_3^-$ | 26 | 22-30 |
| Glucose | 5.6 | 5 |
| Phenol Red | 0.03 | — |
| pH | 7.0-7.4 | 7.4 |

The Earle's balanced salt solution was utilized because it has a pH level and compositional make-up that is similar to plasma. The entire system was contained in a Thermo Fischer 3110 Waterjacket $CO_2$ incubator and maintained at a temperature (about 37° C.), similar to body temperature, for a period of seven weeks.

Figure 9:
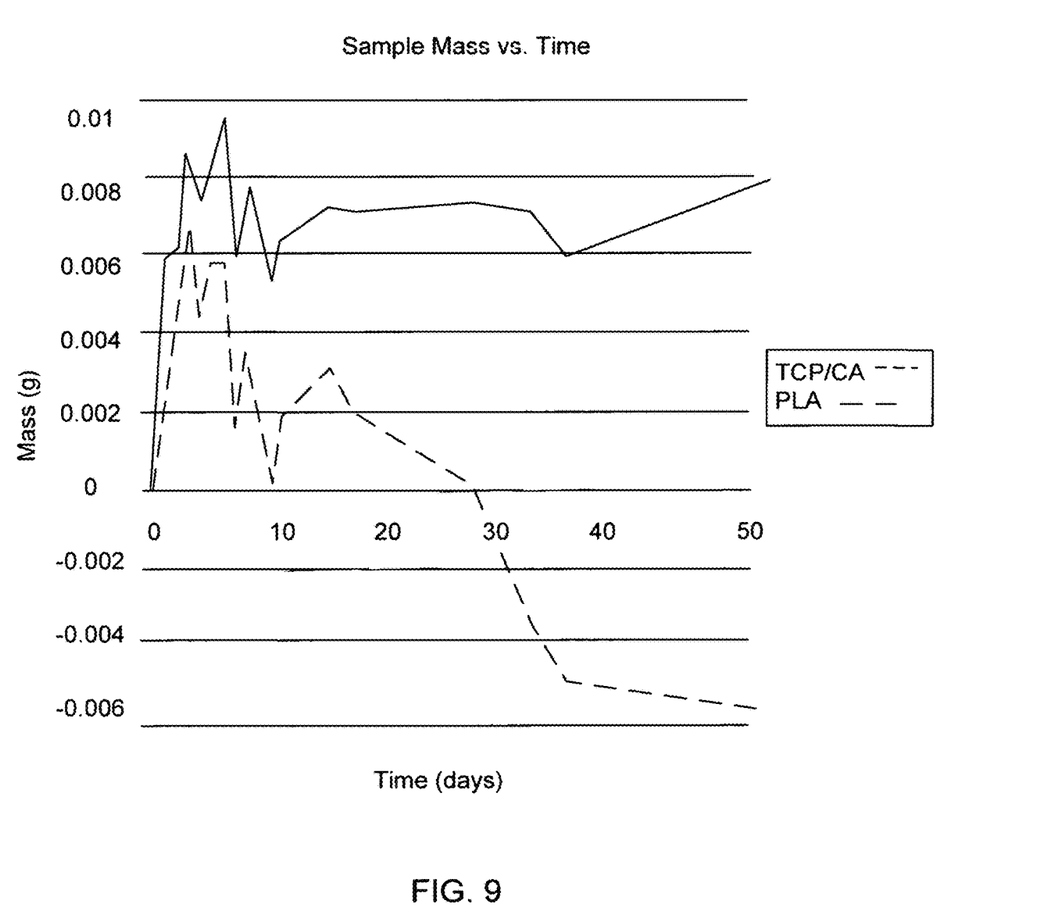
FIG. 9 is a graphical depiction of mass degradation of PLA and TCP during degradation testing in accordance with Example 1, as presented herein.
Figure 10A:
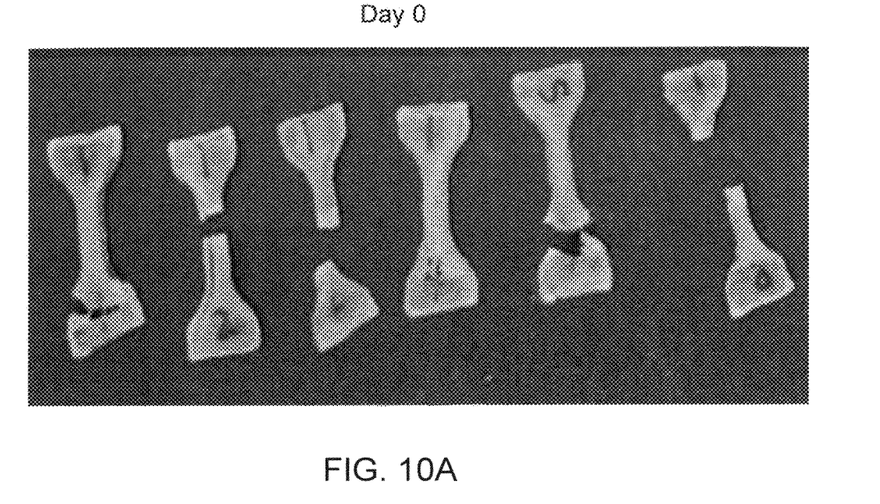
FIG. 10A shows an image of PDLGA samples demonstrating tensile strength prior to degradation testing in accordance with Example 2, presented herein.
Figure 10B:
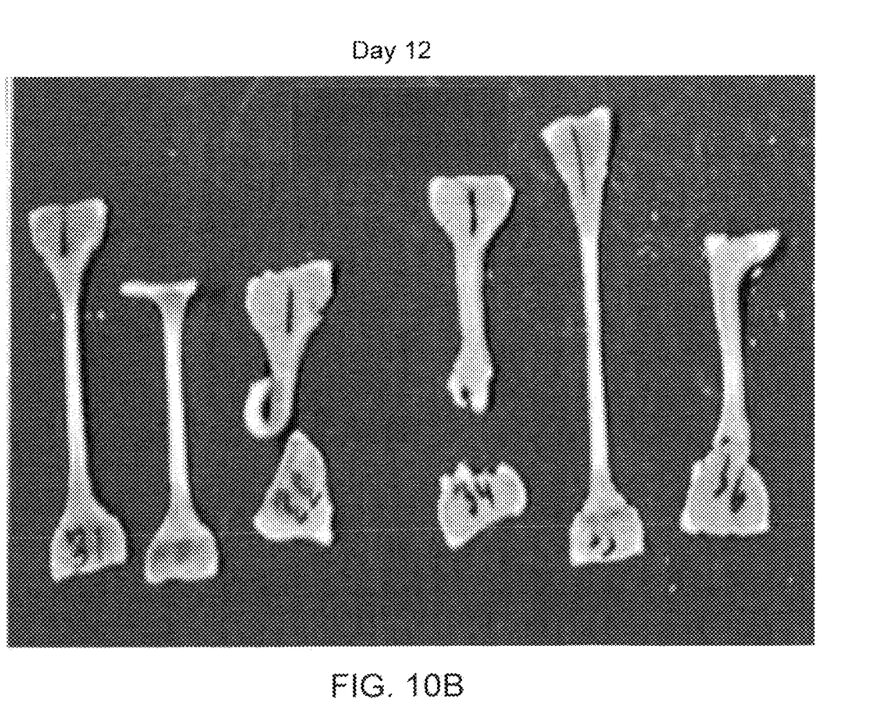
FIG. 10B shows an image of PDLGA samples demonstrating tensile strength following 12 says of degradation testing in accordance with Example 2, presented herein.

During the testing period, the mass degradation of the PLA and TCP was minimal. See FIG. 9. The PLA samples had either an increase in their total mass or a minor decrease in their total mass. Without being limited by theory, the increase may be due to the PLA retaining water. The TCP samples had a decrease in mass of about 0.5% along with pitting after five weeks. These tests indicate that PLA and TCP may not be compatible for use as a bio-erodible coating when applied at the thickness tested and/or at the mixture tested.

Example 2

Tensile Strength and Degradation Testing for PDLGA (85:15), PDLLA, and PLA

Testing was conducted to determine the rate at which bio-erodible polymers, poly-DL-lactide (PDLLA), poly (DL-lactide-co-glycolide) (PDLGA) (85:15 mixture), and polylactic acid (PLA), erode over a course of a few weeks. One millimeter thick sheets of each material were laser cut into ninety-six dogbone shaped (wider at the ends and narrow in the middle) samples for testing.

The dogbone shaped samples were placed in removable trays and positioned in an interconnected four tank system. The samples were held in place on the trays at both ends so that the middle section of the samples was exposed. The four tank system was filled with an Earle's balanced salt solution (see Table 1 above) and a SeaFlow aquatic pump (Model SFDEP1-012-035-21) was connected to the system to induce flow at a flow rate of 0.8 L/min. The entire system was contained in a Thermo Fischer 3110 Waterjacket $CO_2$ incubator maintained at a temperature of about 37° C.

The PDLLA and PLA samples showed minimal visual changes throughout the 8 week testing period and had no significant loss in strength up to day 59. In contrast, the PDLGA samples showed dramatic changes in material property and were completely reduced within two weeks. FIG. 9A shows an image of PDLGA samples that were pulled by tensile force prior to degradation testing, on day 0. Note that the samples were broken with no stretching under tensile force. FIG. 9B shows an image of the PDLGA samples on day 12 of degradation testing. These images illustrate the rapid change in the condition of the PDLGA samples from day 0 to day 12. After a period of 12 days, the PDLGA samples were prone to extensive plastic deformation which allowed them to elongate up to twice their original length before breaking. After 30 days, the PDGLA samples became soft and had low resistance to deformation. The results of this testing indicate that PDGLA is a good material choice for a bio-erodible material in a multi-stage stent presented herein.

It is to be understood that the above-described devices and methods are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A multi-stage stent, comprising:
a stent body comprised of a plurality of interconnected struts compressed in an initial compressed state;
a plurality of bio-erodible expansion stops coupled between a subset of the plurality of struts in a configuration to allow the stent body to expand unimpeded in a first stage expansion from the initial compressed state and to halt expansion of the stent body at a first expansion state,
wherein, as the plurality of bio-erodible expansion stops begin to erode, radial force from the compressed stent body stretches and thins each of the plurality of bio-erodible expansion stops into an hourglass shape until each of the plurality of bio-erodible expansion stops break at a thinned portion of the hourglass shape, thus releasing the stent body from the first expansion state to expand further in a second stage expansion to a fully expanded state.

2. The stent of claim 1, wherein the stent body is comprised of a material selected from the group consisting of carbon nanotubes, carbon infiltrated carbon nanotubes, shape memory materials, polymers, bio-absorbable polymers, steel, stainless steel, nickel, chromium, magnesium, and zinc, including alloys, composites, and combinations thereof.

3. The stent of claim 1, wherein the stent body is comprised of nitinol.

4. The stent of claim 1, wherein the stent body is comprised of carbon infiltrated carbon nanotubes.

5. The stent of claim 1, wherein the bio-erodible material comprises a material selected from the group consisting of polyglycolide (PGA), polylactic acid (PLA), poly-DL-lactide (PDLLA), poly(glyxolide-co-DL-lactide) (PGDLLA), poly(DL-lactide-co-glycolide (PDLGA), poly(lactic-co-glycolic acid) (PLGA), calcium triphosphate, tricalcium phosphate, cyanoacrylate, and magnesium, including composites and combinations thereof.

6. The stent of claim 5, wherein the PDLGA has a ratio of DL-lactic acid to glycolic acid ranging from about 1:1 to about 6:1.

7. The stent of claim 1, wherein the bio-erodible material comprises poly(DL-lactide-co-glycolide (PDLGA).

8. The stent of claim 1, wherein the bio-erodible material is configured to erode over a period of time ranging from about two weeks to about seven weeks in a physiological environment, thereby releasing the stent body from the first expansion state to expand to the fully expanded state by the second stage expansion.

9. The stent of claim 1, wherein the stent body expands radially according to a substantially uniform pattern along an elongate axis of the stent body during expansion from the first expansion state to the fully expanded state.

10. The stent of claim 1, wherein an exterior diameter of the first expansion state is about 70% to about 90% of an exterior diameter of the fully expanded state.

* * * * *